(12) United States Patent
Yamanaka

(10) Patent No.: US 11,141,180 B2
(45) Date of Patent: *Oct. 12, 2021

(54) GRIPPING MECHANISM AND GRIPPING TOOL

(71) Applicant: OLYMPUS CORPORATION, Tokyo (JP)

(72) Inventor: Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 487 days.

This patent is subject to a terminal disclaimer.

(21) Appl. No.: 16/173,335

(22) Filed: Oct. 29, 2018

(65) Prior Publication Data

US 2019/0059922 A1 Feb. 28, 2019

Related U.S. Application Data

(63) Continuation of application No. PCT/JP2016/063728, filed on May 9, 2016.

(51) Int. Cl.
*B25J 15/02* (2006.01)
*A61B 17/29* (2006.01)
(Continued)

(52) U.S. Cl.
CPC .......... *A61B 17/29* (2013.01); *B25J 15/0226* (2013.01); *B25J 15/0233* (2013.01); *B25J 15/08* (2013.01);
(Continued)

(58) Field of Classification Search
None
See application file for complete search history.

(56) References Cited

U.S. PATENT DOCUMENTS 5,507,773 A 4/1996 Huitema et al.
5,562,700 A 10/1996 Huitema et al.
(Continued)

FOREIGN PATENT DOCUMENTS

EP 0668057 A2 8/1995
EP 0800792 A1 10/1997
(Continued)

OTHER PUBLICATIONS

International Search Report and the Written Opinion dated Aug. 9, 2016 received in related International Application No. PCT/JP2016/065962.
(Continued)

*Primary Examiner* — Michael S Lowe
(74) *Attorney, Agent, or Firm* — Scully, Scott, Murphy & Presser, P.C.

(57) ABSTRACT

A gripping mechanism includes: two gripping pieces pivoted relative to each other about a pivot axis; a base supporting the gripping pieces in a pivotable manner; a pulling pulley rotatably supported about a rotation axis parallel to the pivot axis; and a wire wound around the pulley, and causing, with a pulling force, the pulley to move the rotation axis. The pulley is disposed so that a resultant force of tensile forces of the wire becomes greater than the pulling force and generates a moment causing the gripping pieces to be pivoted relative to each other in closing direction. The base includes a first hole. At least one of the gripping pieces includes a second hole inclined in one direction with respect to the longitudinal axis of the first hole. The rotation axis is provided so as to be movable along the longitudinal axes of the individual holes.

7 Claims, 8 Drawing Sheets

(51) Int. Cl.
    *B25J 15/08*     (2006.01)
    *A61B 34/00*     (2016.01)

(52) U.S. Cl.
    CPC ....... *A61B 34/70* (2016.02); *A61B 2017/2927* (2013.01); *A61B 2017/2936* (2013.01); *A61B 2017/2937* (2013.01); *A61B 2017/2939* (2013.01)

(56) References Cited

U.S. PATENT DOCUMENTS

| | | | |
|---|---|---|---|
| 5,562,701 | A | 10/1996 | Huitema et al. |
| 5,562,702 | A | 10/1996 | Huitema et al. |
| 6,206,903 | B1 | 3/2001 | Ramans |
| 6,896,704 | B1 | 5/2005 | Higuchi et al. |
| 7,316,681 | B2 | 1/2008 | Madhani et al. |
| 8,333,780 | B1 * | 12/2012 | Pedros ............... A61B 34/30 606/174 |
| 10,016,207 | B2 | 7/2018 | Suzuki et al. |
| 10,343,291 | B2 | 7/2019 | Jogaski et al. |
| 2002/0040217 | A1 | 4/2002 | Jinno |
| 2004/0267406 | A1 | 12/2004 | Jinno |
| 2006/0167589 | A1 | 7/2006 | Jinno |
| 2007/0288044 | A1 | 12/2007 | Jinno et al. |
| 2008/0039255 | A1 | 2/2008 | Jinno et al. |
| 2008/0232932 | A1 | 9/2008 | Jinno |
| 2009/0110533 | A1 | 4/2009 | Jinno |
| 2009/0112229 | A1 | 4/2009 | Omori et al. |
| 2009/0112230 | A1 | 4/2009 | Jinno |
| 2010/0198253 | A1 | 8/2010 | Jinno et al. |
| 2012/0239011 | A1 | 9/2012 | Hyodo et al. |
| 2014/0249545 | A1 | 9/2014 | Hyodo et al. |
| 2015/0025571 | A1 | 1/2015 | Suzuki et al. |
| 2017/0135710 | A1 | 5/2017 | Hasegawa et al. |
| 2018/0050456 | A1 | 2/2018 | Yamanaka |
| 2019/0231374 | A1 | 8/2019 | Kimura et al. |

FOREIGN PATENT DOCUMENTS

| | | |
|---|---|---|
| EP | 1 195 151 A1 | 4/2002 |
| EP | 1854418 A1 | 11/2007 |
| EP | 1886630 A2 | 2/2008 |
| EP | 2077095 A2 | 7/2009 |
| EP | 2666429 A1 | 11/2013 |
| EP | 2837341 A1 | 2/2015 |
| EP | 3263053 A1 | 1/2018 |
| FR | 1500906 A | 11/1967 |
| JP | H01-199777 A | 8/1989 |
| JP | 2000-325375 A | 11/2000 |
| JP | 2002-102248 A | 4/2002 |
| JP | 2002-103255 A | 4/2002 |
| JP | 2007-301692 A | 11/2007 |
| JP | 2008-036793 A | 2/2008 |
| JP | 2009-106606 A | 5/2009 |
| JP | 2009-107087 A | 5/2009 |
| JP | 2009-107095 A | 5/2009 |
| JP | 2010-221329 A | 10/2010 |
| JP | 2010-227331 A | 10/2010 |
| JP | 2010-253162 A | 11/2010 |
| JP | 2012-187311 A | 10/2012 |
| JP | 2013-215502 A | 10/2013 |
| WO | 2009/057347 A1 | 5/2009 |
| WO | 2010/090292 A2 | 8/2010 |
| WO | WO 2010/126129 A1 | 11/2010 |
| WO | WO 2013/154157 A1 | 10/2013 |
| WO | 2016/136676 A1 | 9/2016 |
| WO | 2016/194777 A1 | 12/2016 |
| WO | WO 2016/194067 A1 | 12/2016 |

OTHER PUBLICATIONS

Office Action dated Apr. 14, 2020 received in U.S. Appl. No. 15/801,356.
International Search Report dated Aug. 18, 2015 issued in PCT/JP2015/065633.
International Search Report dated Aug. 9, 2016 issued in PCT/JP2016/065611.
International Search Report dated Jan. 31, 2017 issued in PCT/JP2016/085237.
German Office Action dated Mar. 13, 2019 in German Patent Application No. 11 2016 001 915.7.
Japanese Office Action dated Jul. 21, 2020 in Japanese Patent Application No. 2017-521884.
International Search Report dated Aug. 2, 2016 issued in PCT/JP2016/063728.
U.S. Office Action dated May 11, 2021 received in U.S. Appl. No. 16/376,685.

* cited by examiner

GRIPPING MECHANISM AND GRIPPING TOOL

CROSS-REFERENCE TO RELATED APPLICATIONS

This is a continuation of International Application PCT/JP2016/063728 which is hereby incorporated by reference herein in its entirety.

TECHNICAL FIELD

The present invention relates to a gripping mechanism and a gripping tool.

BACKGROUND ART

In the related art, there is a known gripping mechanism with which an object such as living tissue is gripped by using a pair of gripping pieces that are joined in a pivotable manner, wherein a toggling mechanism is utilized (for example, see Patent Literature 1). The toggling mechanism is provided with a pair of linkages that are joined so as to be pivotable about a pivot axis shared with the pair of gripping pieces, and an opening motion of the pair of linkages is converted to a closing motion of the pair of gripping pieces. In this structure, it is possible to increase the gripping force exerted by the pair of gripping pieces in accordance with the lengths of the pair of linkages.

CITATION LIST

Patent Literature

{PTL 1} Japanese Unexamined Patent Application, Publication No. 2007-301692

SUMMARY OF INVENTION

A first aspect of the present invention is a gripping mechanism including: two gripping pieces that are pivoted relative to each other about a pivot axis; a base that supports at least one of the gripping pieces at a distal-end portion in a pivotable manner; a pulling pulley that is supported so as to be rotatable about a rotation axis that is parallel to the pivot axis; and a wire that is wound around the pulling pulley, in which one end thereof is secured to one of the gripping pieces or the base, and that causes, with a pulling force applied to the other end thereof, tensile forces that move the rotation axis in one direction to act on both sides of the pulling pulley, between which the rotation axis is interposed, wherein the pulling pulley is disposed so that a resultant force of the tensile forces of the wire acting on the rotation axis becomes greater than the pulling force and generates a moment that causes the gripping pieces to be pivoted in a direction that causes the gripping pieces to be closed relative to each other, the base is provided with a first elongated hole that extends from a distal end toward a proximal end thereof, at least one of the gripping pieces is provided with a second elongated hole that extends, along a plane that is orthogonal to the pivot axis, in a direction that is inclined in one direction with respect to a longitudinal axis of the first elongated hole, and the rotation axis is provided so as to be movable in a direction along longitudinal axial directions of the first elongated hole and the second elongated hole.

DESCRIPTION OF EMBODIMENT

A gripping mechanism 3 and a gripping tool 1 provided with the gripping mechanism 3 according to an embodiment of the present invention will be described below with reference to the drawings.

Figure 1:
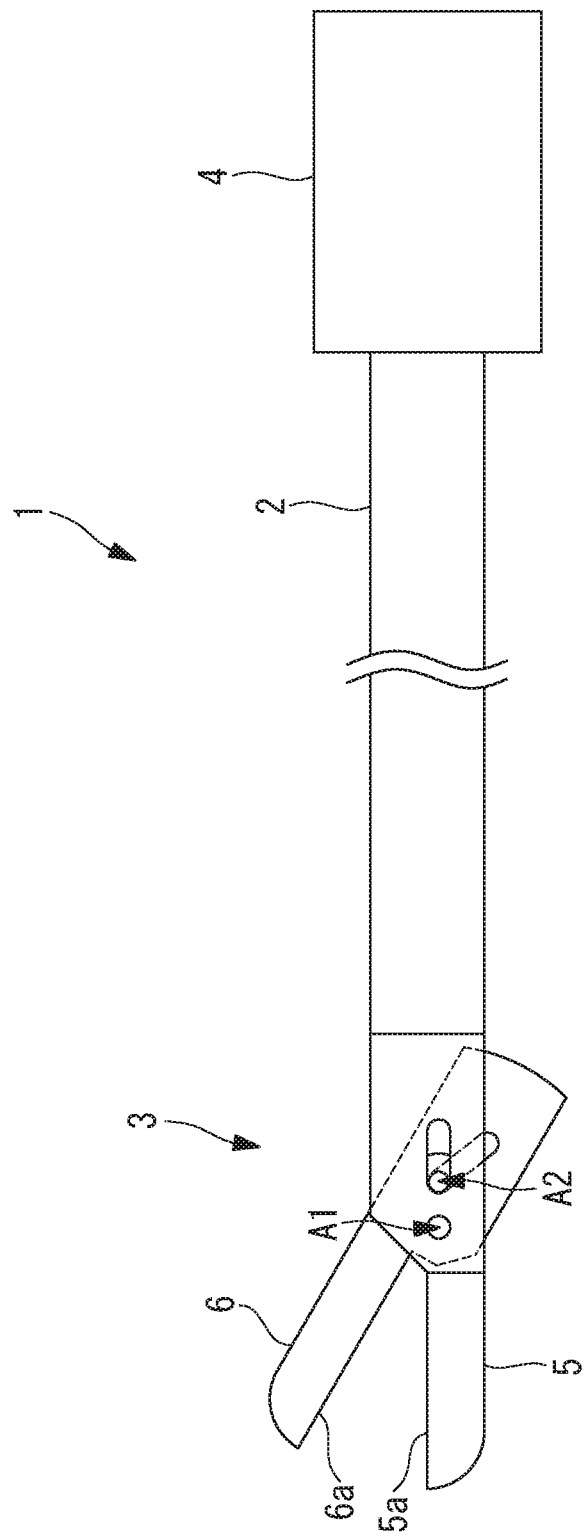
FIG. 1 is an overall configuration diagram showing a gripping tool according to an embodiment of the present invention.

The gripping tool 1 according to this embodiment is a medical equipment that is used when gripping a subject such as living tissue. As shown in FIG. 1, the gripping tool 1 includes: an elongated body portion (base) 2 that can be inserted into a body; the gripping mechanism 3 that is provided at a distal end of the body portion 2; and a driving portion 4 that is connected to a proximal end of the body portion 2.

Figure 2:
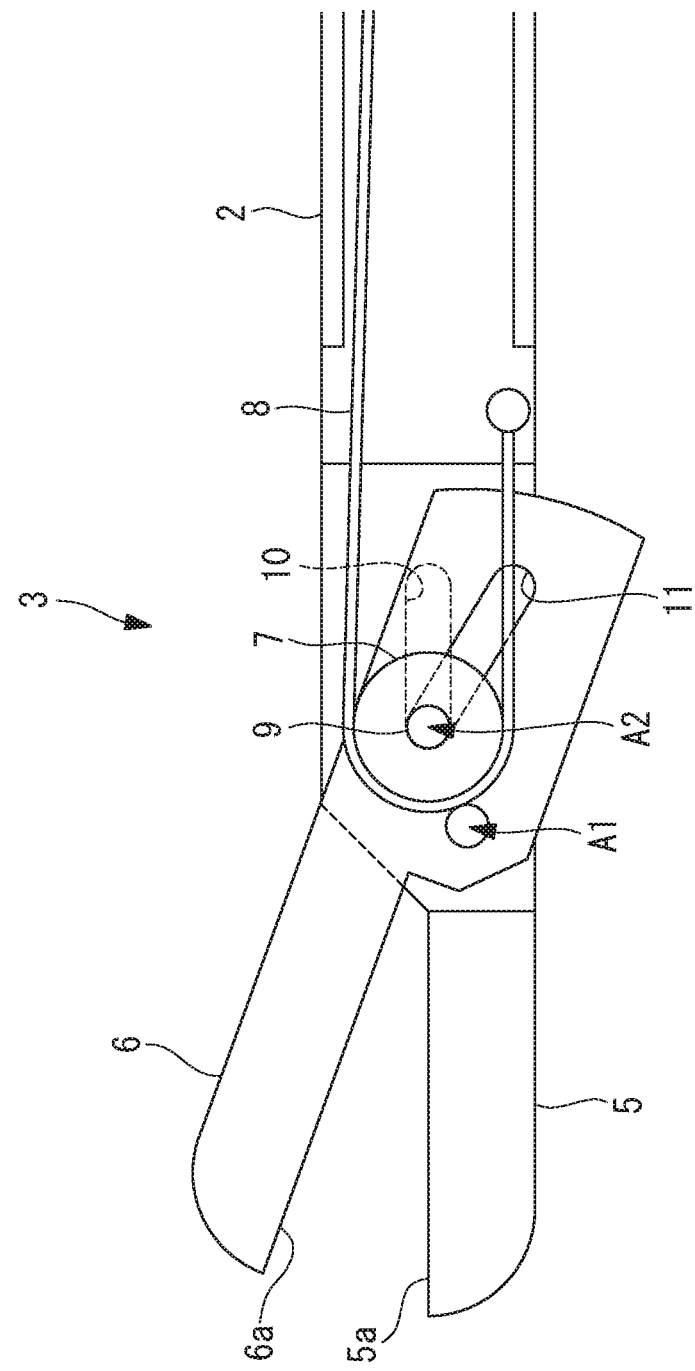
FIG. 2 is a longitudinal cross-sectional view showing a state in which two gripping pieces of a gripping mechanism according to a first embodiment of the present invention are open.
Figure 3:
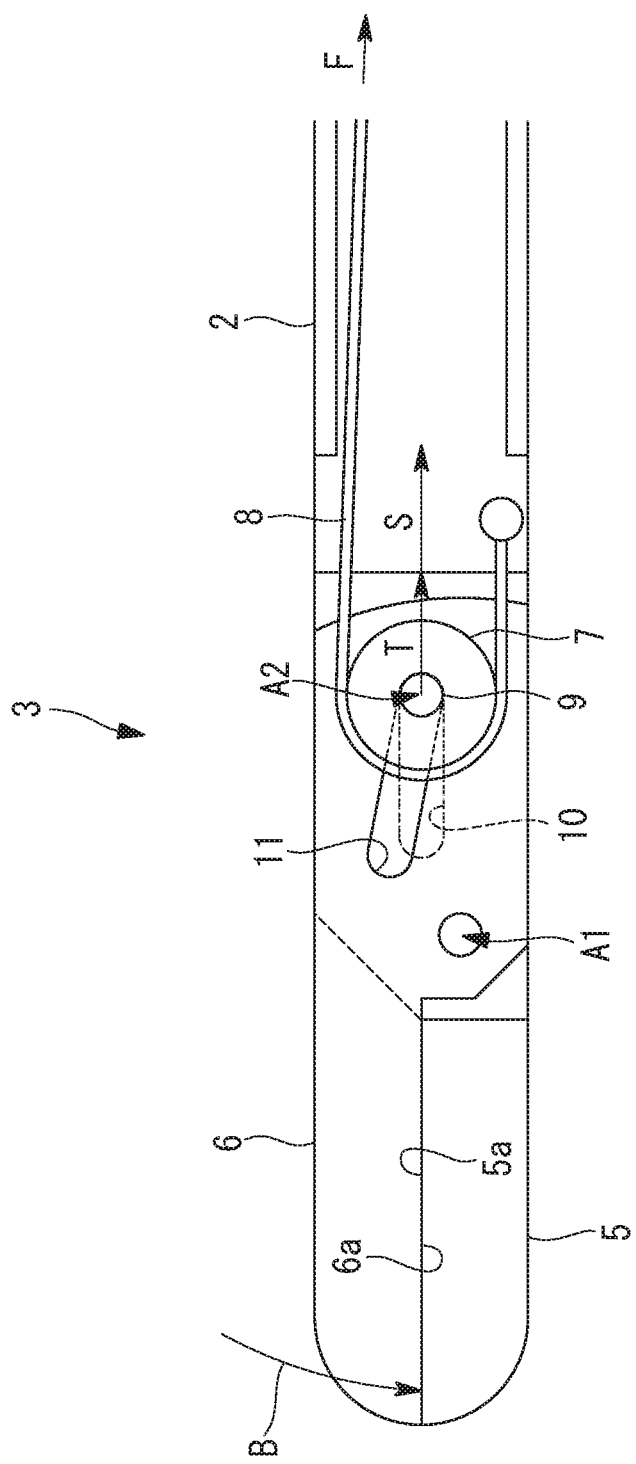
FIG. 3 is a longitudinal cross-sectional view showing a state in which the two gripping pieces of the gripping mechanism in FIG. 2 are closed.

As shown in FIGS. 2 and 3, the gripping mechanism 3 according to this embodiment includes a first gripping piece 5, a second gripping piece 6, a pulling pulley 7, and a wire 8. The first gripping piece 5 is secured to the body portion 2. The second gripping piece 6 is joined with the first gripping piece 5 so as to be pivotable about a pivot axis A1 that is orthogonal to the longitudinal axis of the body portion 2. The pulling pulley 7 is supported by the second gripping piece 6 so as to be rotatable about a rotation axis A2 that is parallel to the pivot axis A1. The wire 8 is wound around the pulling pulley 7. FIG. 2 shows a closed state in which the second gripping piece 6 is closed with respect to the first gripping piece 5.

The first gripping piece 5 has a first gripping surface 5a on a distal-end side thereof, and the second gripping piece 6 has a second gripping surface 6a on a distal-end side thereof. The first gripping piece 5 and the second gripping piece 6 are individually disposed in directions along the longitudinal direction of the body portion 2 so that the gripping surfaces 5a and 6a face each other.

The pivot axis A1 that connects the second gripping piece 6 to the first gripping piece 5 in a pivotable manner is disposed farther on the proximal-end side than the first gripping surface 5a and the second gripping surface 6a are. As a result of the second gripping piece 6 pivoting about the pivot axis A1, the distal ends of the first gripping piece 5 and second gripping piece 6 are opened and closed.

The pulling pulley 7 is supported, in a rotatable manner, by a shaft 9, which is co-axial with the rotation axis A2 of the pulling pulley 7, farther on the proximal-end side than the pivot axis A1 of the second gripping piece 6 is.

The body portion 2 to which the first gripping piece 5 is secured is provided with a first elongated hole 10 that has a longitudinal axis that extends in a front-to-rear direction, and the second gripping piece 6 is provided with a second elongated hole 11 that has a longitudinal axis 11a that is inclined with respect to the longitudinal axis 10a of the first elongated hole 10. The shaft 9 is disposed so as to pass through both of the elongated holes 10 and 11 at the position at which the two elongated holes 10 and 11 intersect each other.

The wire 8 is disposed inside the body portion 2 in the longitudinal direction thereof, and, after a distal-end portion thereof is wound approximately half way around the pulling pulley 7 on a distal-end side thereof on an outer circumferential surface, the distal end thereof is secured to the body portion 2 farther on the proximal-end side than the rotation axis A2 is. The proximal end of the wire 8 is connected to the driving portion 4.

The parts of the wire 8 that are wound substantially half way around the pulling pulley 7 and that extend in two tangential directions of the pulling pulley 7 are disposed so as to be substantially parallel to each other.

The driving portion 4 has a motor (not shown) connected to the proximal end of the wired 8, and a tensile force is generated in the wire 8 by pulling the wire 8 toward the proximal end by the motor.

Figure 4:
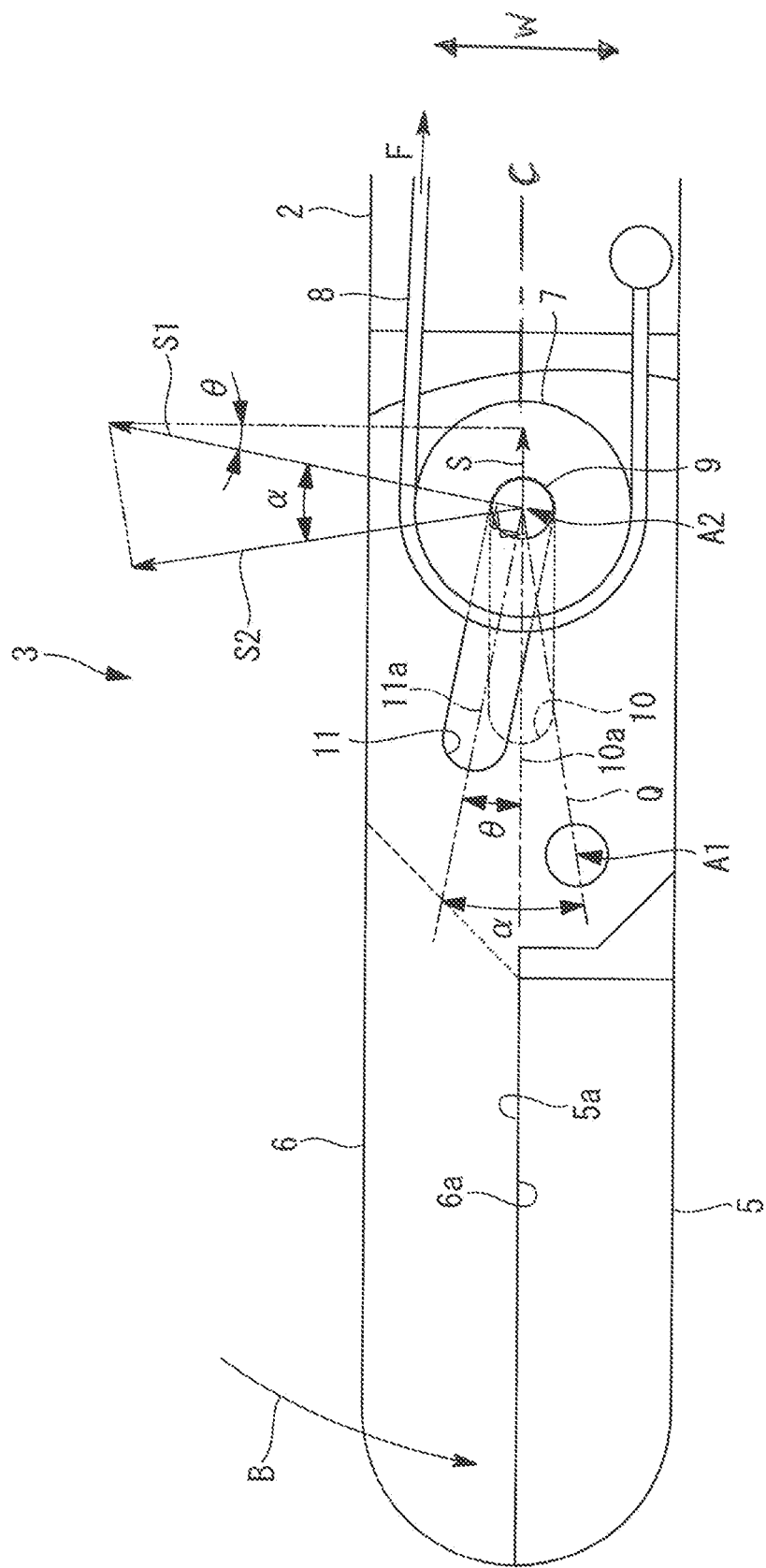
FIG. 4 is a diagram for explaining, in the state in FIG. 3, a resultant force that acts on a pulling pulley and a moment that causes the second gripping piece to slide.

As shown in FIG. 4, in this embodiment, the first elongated hole 10 provided in the body portion 2 is provided in a straight manner along the longitudinal direction of the body portion 2 at substantially the center C of the body portion 2 in the width direction W.

In addition, an angle θ formed between the longitudinal axis 10a of the first elongated hole 10 and the longitudinal axis 11a of the second elongated hole 11, and an angle α formed between a line segment Q connecting the pivot axis A1 and the rotation axis A2 and the longitudinal axis 11a of the second elongated hole 11 satisfy the following relational expression:

$$\cos \alpha / \sin \theta > 1 \qquad (1).$$

The operations of the thus-configured gripping mechanism 3 and gripping tool 1 according to this embodiment are described below.

With the gripping tool 1 according to this embodiment, as a result of the wire 8 being pulled toward the proximal end by operating the driving portion 4, tensile forces that are substantially equal to a pulling force F are generated in the individual portions of the wire 8.

Because substantially equal tensile forces T are also individually generated in the two portions of the wired 8 that are disposed so as to be substantially parallel to each other with the rotation axis A2 of the pulling pulley 7 existing therebetween, as shown in FIG. 3, a resultant force S whose magnitude is two times greater than that of the tensile force T acts on the rotation axis A2 of the pulling pulley 7. Therefore, the pulling force is amplified twofold as a result.

Here, of the resultant force S, a resultant force component S1 that is orthogonal to the longitudinal axis 11a of the second elongated hole 11 serves as the force that causes the second gripping piece 6 to be pivoted with respect to the first gripping piece 5, and, of the resultant force component S1, the product of an orthogonal component S2 that is orthogonal to the line segment Q connecting the pivot axis A1 and the rotation axis A2 and the size of the line segment Q serves as the moment that causes the second gripping piece 6 to be pivoted with respect to the first gripping piece 5.

In other words, the resultant force component S1 can be expressed as:

$$S1 \cdot \sin \theta = S \qquad (2), \text{ and}$$

the orthogonal component S2 can be expressed as:

$$S2 = S1 \cdot \cos \alpha \qquad (3).$$

Therefore, if $$S2 > S \qquad (4),$$

it is possible to generate the orthogonal component S2 in which the resultant force S is amplified, because of the positional relationship between the pivot axis A1 and the angles α and θ of the two elongated holes 10 and 11.

By substituting Expressions (2) and (3) into Expression (4), it is possible to achieve the relationship in Expression (1). As a result, the gripping mechanism 3 according to this embodiment can achieve the resultant force S in which the pulling force F is amplified twofold by the action of the pulling pulley 7, and, because Expression (1) is satisfied, there is an advantage in that it is possible to generate a moment in which the resultant force S is additionally amplified.

In the example shown in FIGS. 3 and 4, as indicated by the arrow B, a counterclockwise moment acts on the second gripping piece 6, the second gripping piece 6 is pivoted counterclockwise about the pivot axis A1 with respect to the first gripping piece 5, and thus, the gripping surfaces 5a and 6a are closed with respect to each other. Thus, as shown in FIG. 3, it is possible to grip tissue between gripping surfaces 5a and 6a of the first gripping piece 5 and the second gripping piece 6.

In this case, with the gripping mechanism 3 according to this embodiment, it is possible, by means of the pulling pulley 7 and the elongated holes 10 and 11, to generate the moment that causes the second gripping piece 6 to be pivoted with a force that is amplified more than substantially twofold relative to the pulling force F applied to the proximal end of the wire 8. In other words, there is an advantage in that it is possible to firmly grip the tissue with a large force even if the pulling force F applied to the proximal end of the wire 8 is small.

Note that, in this embodiment, the angle α formed between the line segment Q connecting the pivot axis A1 and the rotation axis A2 and the longitudinal axis 11a of the second elongated hole 11 needs to be α<90° regardless of the pivoting angular position at which the second gripping piece 6 is disposed with respect to the first gripping piece 5. In the case in which α=90°, a singular point is formed, and thus, it is not possible to generate the moment in the direction that causes the two gripping pieces to be closed.

By always achieving α<90°, it is possible to stably realize the closing motion.

In addition, with the gripping mechanism 3 according to this embodiment, because the pulling pulley 7 is disposed at substantially the center of the body portion 2 in the width direction and the first elongated hole 10, which defines the sliding pathway of the pulling pulley 7, linearly extends along the longitudinal direction of the body portion 2, there is an advantage in that it is possible to reduce the diameter of the gripping tool 1 by minimizing the influences on the outer diameter of the pulling pulley 7, which limits the outer diameter of the gripping tool 1.

In addition, in this embodiment, as shown in FIGS. 1 to 4, the pivot axis A1 is disposed by being offset, with respect to the longitudinal axis 10a of the first elongated hole 10, farther in the direction in which the second gripping piece 6 closes with respect to the first gripping piece 5. By doing so, it is possible to ensure a large enough space in the portion closer to the second gripping piece 6 than the pivot axis A1 of the first gripping piece 5, and thus, it is possible to ensure a large enough space for disposing a wire (not shown) for opening the gripping pieces 5 and 6, as well as other equipment such as a sensor, etc.

Figure 5:
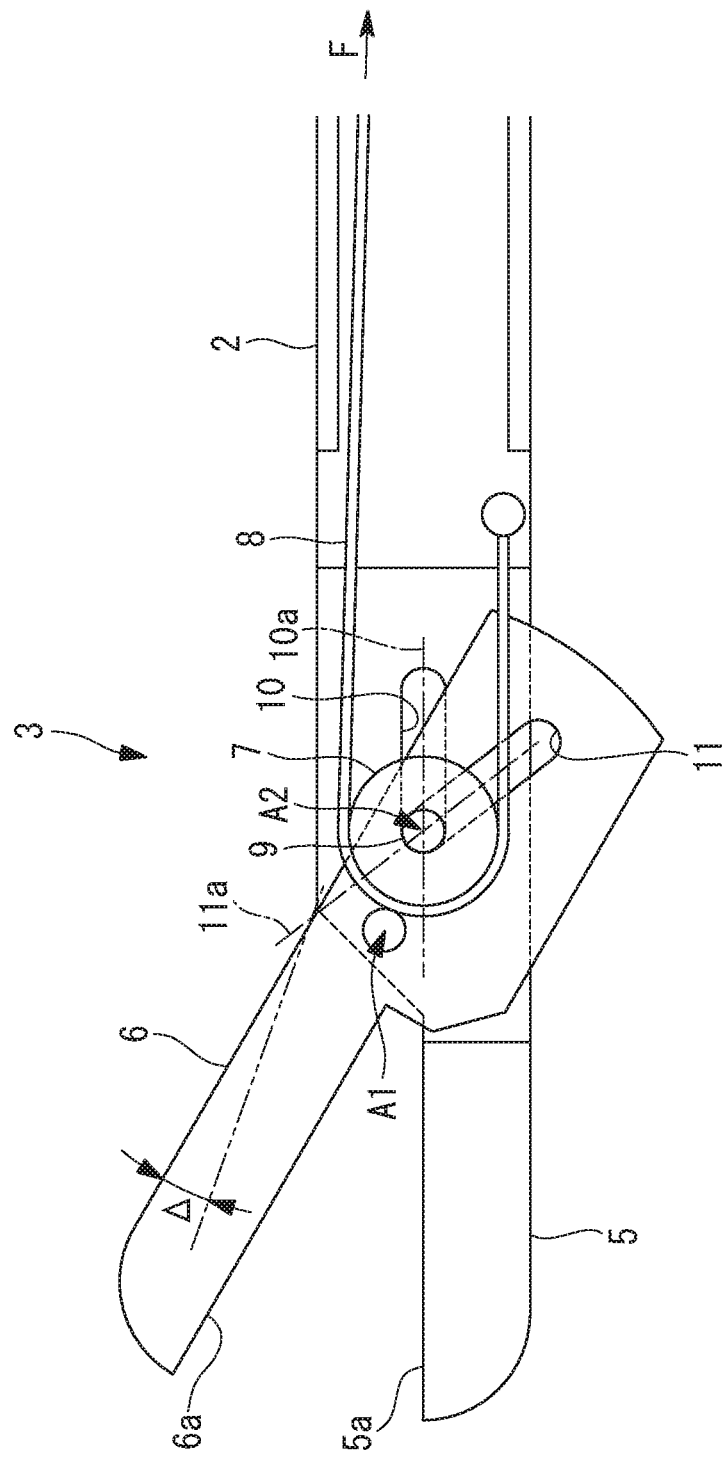
FIG. 5 is a longitudinal cross-sectional view showing a state in which two gripping pieces of a modification of the gripping mechanism in FIG. 2 are open.
Figure 6:
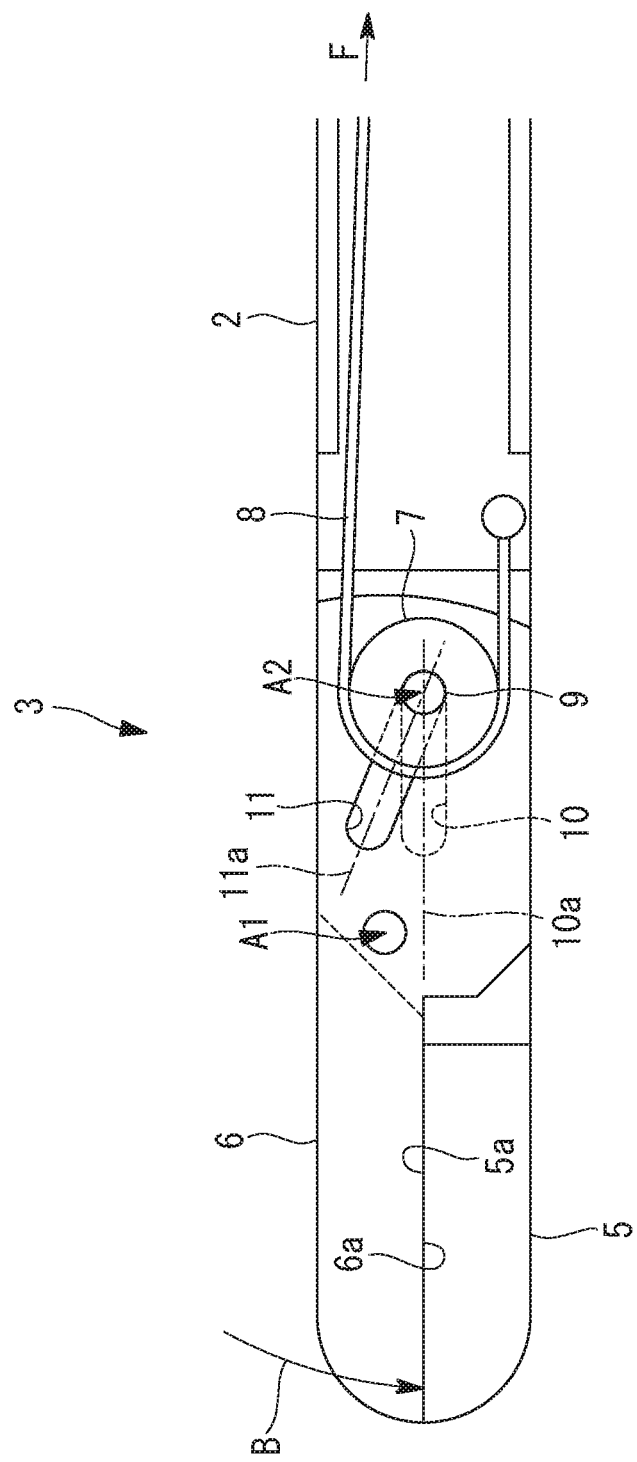
FIG. 6 is a longitudinal cross-sectional view showing a state in which the two gripping pieces of the gripping mechanism in FIG. 5 are closed.

Alternatively, as shown in FIGS. 5 and 6, the pivot axis A1 may be disposed by being offset, with respect to the longitudinal axis 10a of the first elongated hole 10, farther in the direction in which the second gripping piece 6 opens with respect to the first gripping piece 5. By doing so, as indicated by the reference sign A in FIG. 5, it is possible to increase the angle at which the second gripping piece 6 is opened with respect to the first gripping piece 5 by an amount corresponding to the degree of offset.

In addition, it is preferable that the pivot axis A1 be disposed between a distal-end-side extension of the longitudinal axis 10a of the first elongated hole 10 and a distal-end-side extension of the line segment Q connecting the pivot axis A1 and the rotation axis A2. As a result of the pivot axis A1 being offset farther in the direction of the extension of the longitudinal axis 11a of the second elongated hole 11 with respect to the extension of the longitudinal axis 10a of the first elongated hole 10, it is possible to increase the angle at which the two gripping pieces 5 and 6 are opened with respect to each other, as described above, and, as a result of the pivot axis A1 being brought close to the extension of the longitudinal axis 11a of the second elongated hole 11, it is possible to increase the moment that causes the two gripping pieces 5 and 6 to be closed relative to each other.

Figure 7:
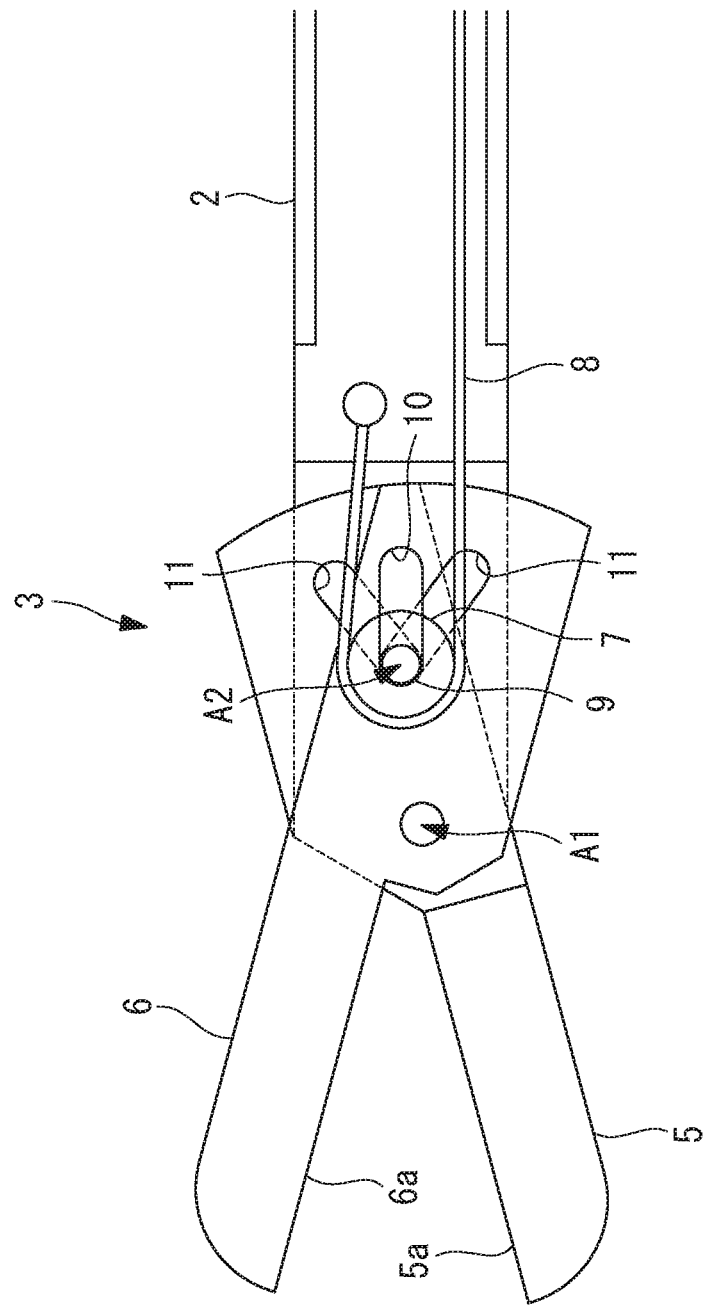
FIG. 7 is a longitudinal cross-sectional view showing a state in which two gripping pieces of another modification of the gripping mechanism in FIG. 2 are open.
Figure 8:
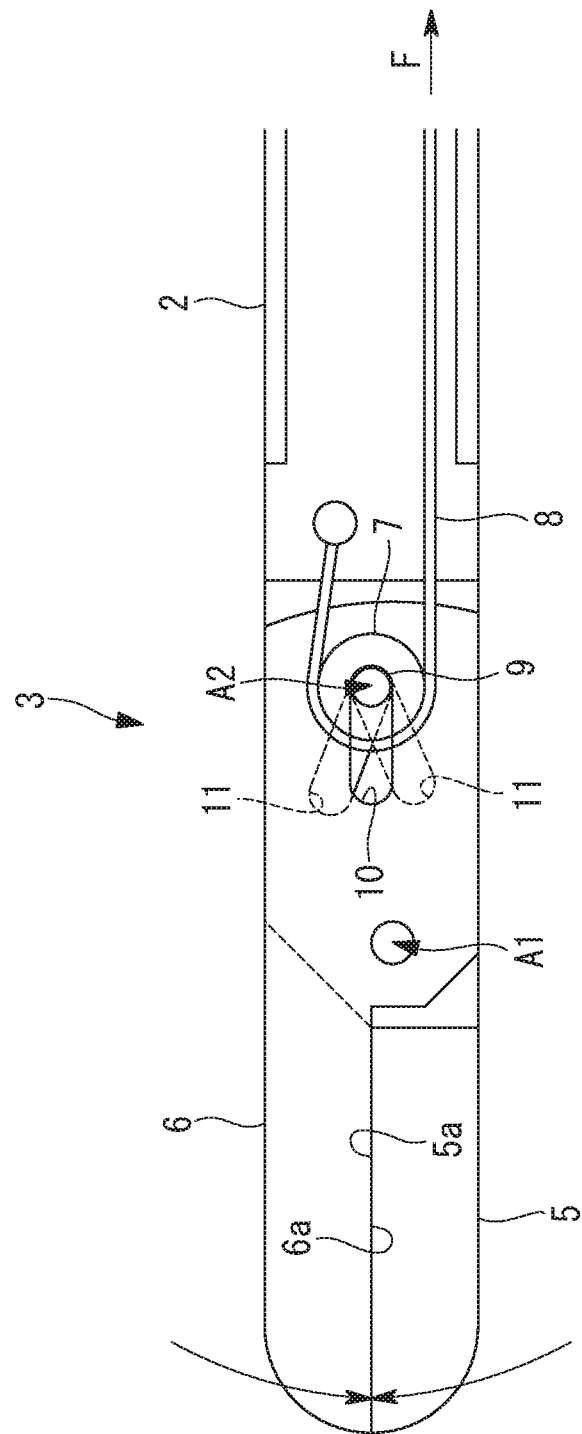
FIG. 8 is a longitudinal cross-sectional view showing a state in which the two gripping pieces of the gripping mechanism in FIG. 7 are closed.

In addition, although this embodiment has been described in terms of the case in which the first gripping piece 5 is secured to the body portion 2 and only the second gripping piece 6 is pivoted about the pivot axis A1, alternatively, as shown in FIGS. 7 and 8, both the first gripping piece 5 and the second gripping piece 6 may be supported by the body portion 2 so as to be pivotable about the pivot axis A1.

In this case, the second elongated holes 11 that are inclined with respect to the first elongated hole 10 may be provided in both the first gripping piece 5 and the second gripping piece 6, and the longitudinal axes 11a of the two second elongated holes 11 of the gripping pieces 5 and 6 may be inclined in the opposite direction from the longitudinal axis 10a of the first elongated hole 10.

In this case also, by disposing both of the second elongated holes 11 provided in the gripping pieces 5 and 6 so as to satisfy the relationship in the above-described Expression (1), just by applying a small pulling force F, it is possible to firmly grip, with a large gripping force, the subject, such as tissue, between the two gripping surfaces 5a and 6a by generating the moment by additionally amplifying the resultant force S in which the pulling force F applied on the proximal-end side of the wire 8 is amplified approximately twofold by the pulling pulley 7. In addition, by distributing the pivoting angle between the two gripping pieces 5 and 6, it is possible to ensure the angle at which the gripping pieces 5 and 6 are opened is large enough.

In addition, in this embodiment, because two portions of the wire 8 wound around the pulling pulley 7 are disposed so as to be substantially parallel to each other, it is possible to cause a force that is twice as great as the pulling force F exerted on the wire 8 to act on the pulling pulley 7; however, there is no limitation thereto. In other words, because the resultant force S of the tensile forces T becomes equal to the pulling force F when the relative angle of the two portions of the wire 8 is 120°, there is an advantage in that it is possible to amplify the pulling force F so long as the two portions of the wire 8 form an angle that is less than 120°. However, in order to achieve an elongated shape of the gripping tool 1, it is preferable that the two portions of the wire 8 be disposed so as to be substantially parallel to each other.

In addition, although this embodiment has been described in terms of the case in which the wire 8 is wound substantially half way around the pulling pulley 7, for example, a return pulley (not shown) having a rotation axis that is parallel to the rotation axis A2 may be provided, and the wire 8 may be wound more than once between the pulling pulley 7 and the return pulley. By doing so, there is an advantage in that it is possible to additionally amplify the pulling force F.

The above-described embodiment leads to the following invention.

A first aspect of the present invention is a gripping mechanism including: two gripping pieces that are pivoted relative to each other about a pivot axis; a base that supports at least one of the gripping pieces at a distal-end portion in a pivotable manner; a pulling pulley that is supported so as to be rotatable about a rotation axis that is parallel to the pivot axis; and a wire that is wound around the pulling pulley, in which one end thereof is secured to one of the gripping pieces or the base, and that causes, with a pulling force applied to the other end thereof, tensile forces that move the rotation axis in one direction to act on both sides of the pulling pulley, between which the rotation axis is interposed, wherein the pulling pulley is disposed so that a resultant force of the tensile forces of the wire acting on the rotation axis becomes greater than the pulling force and generates a moment that causes the gripping pieces to be pivoted in a direction that causes the gripping pieces to be closed relative to each other, the base is provided with a first elongated hole that extends from a distal end toward a proximal end thereof, at least one of the gripping pieces is provided with a second elongated hole that extends, along a plane that is orthogonal to the pivot axis, in a direction that is inclined in one direction with respect to a longitudinal axis of the first elongated hole, and the rotation axis is provided so as to be movable in a direction along longitudinal axial directions of the first elongated hole and the second elongated hole.

With this aspect, when the pulling force is applied to the other end of the wire, tensile forces that are equal to the pulling force are generated in the wire, and the resultant force of the tensile forces acting in the longitudinal direction of both sides of the wire between which the rotation axis exists is applied to the pulling pulley around which the wire is wound. As a result of this resultant force generating the moment about the pivot axis in the direction that causes at least one of the gripping pieces to be closed, the two gripping pieces are closed relative to each other, and thus, it is possible to grip a subject, such as tissue, disposed therebetween.

In this case, with this aspect, the pulling pulley is disposed so that the resultant force that acts on the pulling pulley becomes greater than the pulling force. In other words, by disposing the pulling pulley so that the relative angle of the wire that extends in the tangential directions of the pulling pulley on both sides thereof between which the rotation axis exists becomes less than 120°, it is possible to apply an amplified force as compared to the case in which the pulling force is directly applied at the position of the rotation axis without involving the pulling pulley.

Furthermore, as a result of the resultant force component that is orthogonal to the longitudinal axis of the second elongated hole pushing the second elongated hole in the direction that is orthogonal to the longitudinal axis, the moment is generated about the pivot axis, and thus, the two gripping pieces are pivoted relative to each other. Because the resultant force in which the pulling force is amplified is used, it is possible to cause, even with a small pulling force, the two gripping pieces to be pivoted in direction that causes two gripping pieces to be closed with a large moment, thereby gripping the subject, such as tissue or the like, with a large force.

In the above-described aspect, in the state in which the two gripping pieces are closed, the following conditional expression may be satisfied:

$$\cos \alpha / \sin \theta > 1,$$

where $\theta$ is an angle formed between the longitudinal axis of the first elongated hole and the longitudinal axis of the second elongated hole, and $\alpha$ is an angle formed between a line segment connecting the rotation axis and the pivot axis and the longitudinal direction of the second elongated hole.

By doing so, it is possible to apply the force of the component in which the resultant force applied to the rotation axis is additionally amplified in the direction that is orthogonal to the line segment connecting the rotation axis and the pivot axis, and, in conjunction with the amplification of the pulling force by the pulling pulley, it is possible to cause the two gripping pieces to be moved relative to each other in the direction that causes the two gripping pieces to be closed with the large moment.

In addition, in the above-described aspect, an angle formed between a line segment connecting the rotation axis and the pivot axis and the longitudinal axis of the second elongated hole may be less than 90°.

By doing so, it is possible to always generate a moment in the direction that causes the two gripping pieces to be closed without forming a singular point.

In addition, in the above-described aspect, the first elongated hole may be provided at a substantially center of the base in the width direction so as to be parallel to a longitudinal axis of the base.

By doing so, it is possible to dispose the pulling pulley, which is moved along the longitudinal axis of the first elongated hole, at substantially the center of the base in the width direction, and thus, it is possible to reduce the diameter of the gripping mechanism.

In addition, in the above-described aspect, the pivot axis may be disposed between a distal-end-side extension of the longitudinal axis of the first elongated hole and a distal-end-side extension of the longitudinal axis of the second elongated hole.

By doing so, as a result of the pivot axis being offset farther in the direction of the extension of the longitudinal axis of the second elongated hole with respect to the longitudinal axis of the first elongated hole, it is possible to increase the angle at which the two gripping pieces are opened. In addition, as a result of the pivot axis being brought close to the extension of the longitudinal axis of the second elongated hole, it is possible to increase the moment that causes the two gripping pieces to be closed relative to each other.

In addition, in the above-described aspect, the wire may be wound around the pulling pulley at least once.

By doing so, with an increase in the number of times the wire is wound around the pulling pulley, it is possible to increase the resultant force of the tensile forces exerted on the pulling pulley.

In addition, in the above-described aspect, the two gripping pieces may be individually supported by the base so as to be pivotable about the pivot axis, and, the second elongated hole provided in each of the gripping pieces may be provided so as to be inclined in an opposite direction with respect to the longitudinal axis of the first elongated hole.

By doing so, by applying the pulling force to the wire in one direction, it is possible to apply the moment in the opposite direction to the two gripping pieces, and thus, it is possible to grip the subject by causing both of the gripping pieces to be pivoted.

In addition, another aspect of the present invention is a gripping tool including: any one of the above-described gripping mechanisms; and a driving portion that is connected to the gripping mechanism and that generates the pulling force.

With this aspect, by generating the pulling force by operating the driving portion, it is possible to close the two gripping pieces relative each other with a smaller pulling force.

REFERENCE SIGNS LIST 1 gripping tool
2 body portion (base)
3 gripping mechanism
4 driving portion
5 first gripping piece (gripping piece)
6 second gripping piece (gripping piece)
7 pulling pulley
8 wire
10 first elongated hole
10a, 11a longitudinal axis
11 second elongated hole
A1 pivot axis
A2 rotation axis

The invention claimed is:
1. A gripping mechanism comprising:
two gripping pieces that are pivoted relative to each other about a pivot axis;
a base that supports at least one of the two gripping pieces at a distal-end portion in a pivotable manner;
a pulling pulley that is supported so as to be rotatable about a rotation axis that is parallel to the pivot axis; and
a wire that is wound around the pulling pulley, in which one end of the wire is secured to one of the two gripping pieces or the base, and that causes, with a pulling force applied to an other end of the wire, tensile forces that move the rotation axis in one direction to act on both sides of the pulling pulley, between which the rotation axis is interposed,
wherein the pulling pulley is disposed so that a resultant force of the tensile forces of the wire acting on the rotation axis becomes greater than the pulling force and generates a moment that causes the two gripping pieces to be pivoted in a direction that causes the two gripping pieces to be closed relative to each other, the base is provided with a first elongated hole that extends from a distal end toward a proximal end of the base, at least one of the two gripping pieces is provided with a second elongated hole that extends, along a plane that is orthogonal to the pivot axis, in a direction that is inclined in one direction with respect to a longitudinal axis of the first elongated hole, and the rotation axis is provided so as to be movable in a direction along longitudinal axial directions of the first elongated hole and the second elongated hole;

wherein, in the state in which the two gripping pieces are closed, the following conditional expression is satisfied:

$\cos \alpha / \sin \theta > 1$, where $\theta$ is an angle formed between the longitudinal axis of the first elongated hole and a longitudinal axis of the second elongated hole, and $\alpha$ is an angle formed between a line segment that connects the rotation axis and the pivot axis and the longitudinal direction of the second elongated hole.

2. A gripping mechanism according to claim 1, wherein the angle formed between the line segment connecting the rotation axis and the pivot axis and the longitudinal axis of the second elongated hole is less than 90°.

3. A gripping mechanism according to claim 1, wherein the first elongated hole is provided at substantially center of the base in a width direction so as to be parallel to a longitudinal axis of the base.

4. A gripping mechanism according to claim 1, wherein the pivot axis is disposed between a distal-end-side extension of the longitudinal axis of the first elongated hole and a distal-end-side extension of the longitudinal axis of the second elongated hole.

5. A gripping mechanism according to claim 1, wherein the wire is wound around the pulling pulley at least once.

6. A gripping mechanism according to claim 1, wherein the two gripping pieces are individually supported by the base so as to be pivotable about the pivot axis, and the second elongated hole provided in each of the two gripping pieces is provided so as to be inclined in an opposite direction with respect to the longitudinal axis of the first elongated hole.

7. A gripping tool that comprising:

a gripping mechanism according to claim 1; and a driving portion that is connected to the gripping mechanism and that generates the pulling force.

* * * * *